US011931175B2

(12) United States Patent
Pintat et al.

(10) Patent No.: US 11,931,175 B2
(45) Date of Patent: Mar. 19, 2024

(54) IN-EAR AND AROUND-THE-EAR ELECTROENCEPHALOGRAPHY SYSTEM WITH FLOATING ELECTRODES AND METHOD THEREOF

(71) Applicant: ECOLE DE TECHNOLOGIE SUPERIEURE, Montreal (CA)

(72) Inventors: Valentin Pintat, Montreal (CA); Jeremie Voix, Montreal (CA); Gabrielle Cretot-Richert, Montreal (CA); Guilhem Viallet, Montreal (CA); Aidin Delnavaz, Lachine (CA)

(73) Assignee: ECOLE DE TECHNOLOGIE SUPERIEURE, Montreal (CA)

( * ) Notice: Subject to any disclaimer, the term of this patent is extended or adjusted under 35 U.S.C. 154(b) by 581 days.

(21) Appl. No.: 16/713,353

(22) Filed: Dec. 13, 2019

(65) Prior Publication Data

US 2021/0177352 A1    Jun. 17, 2021

(51) Int. Cl.
*A61B 5/00* (2006.01)
*A61B 5/291* (2021.01)
*A61B 5/318* (2021.01)
*A61B 5/398* (2021.01)

(52) U.S. Cl.
CPC ............ *A61B 5/6817* (2013.01); *A61B 5/291* (2021.01); *A61B 5/318* (2021.01); *A61B 5/398* (2021.01); *A61B 2560/0406* (2013.01); *A61B 2562/0215* (2017.08)

(58) Field of Classification Search
CPC .............. A61B 5/25–256; A61B 5/279; A61B 5/6815–6817
See application file for complete search history.

(56) References Cited

U.S. PATENT DOCUMENTS

| 9,408,552 B2* | 8/2016 | Kidmose ................ B33Y 80/00 |
| 10,213,157 B2 | 2/2019 | Farrell et al. |
| 2012/0123290 A1 | 5/2012 | Kidmose et al. |
| 2012/0302858 A1 | 11/2012 | Kidmose et al. |
| 2017/0281037 A1 | 10/2017 | Kidmose et al. |
| 2018/0177421 A1 | 6/2018 | Kilsgaard et al. |

(Continued)

FOREIGN PATENT DOCUMENTS

EP        3181041 A1    6/2017

*Primary Examiner* — Scott M. Getzow
(74) *Attorney, Agent, or Firm* — Brouillette Legal Inc.; Robert Brouillette

(57) ABSTRACT

A system for reading bioelectrical signals from the skin of a user is provided. The system comprises a plug for inserting in an ear having an inner portion to be inserted into the ear, an outer portion and an inner floating electrode comprising a floating conductive wire, the floating conductive wire being attached to the inner portion of the plug, disposed over the outskirt of the outer portion and in communication with the signal processor. The system further comprises an outer floating electrode for reading a signal from skin around the ear, the floating electrode comprising a floating conductive portion connected to the plug and being in communication with the signal processor, a resilient portion adapted to expand and retract the floating conductive portion and a non-conductive linking portion attached to the floating conductive portion. The floating, resilient and non-conductive linking portions form an expandable loop around the ear from the plug.

21 Claims, 5 Drawing Sheets

(56) References Cited

U.S. PATENT DOCUMENTS

2019/0053756 A1    2/2019  Ayers et al.
2019/0380606 A1*  12/2019  Yoshida .............. H01M 50/538
2020/0085369 A1*  3/2020  Vu ........................ A61B 5/398

* cited by examiner

IN-EAR AND AROUND-THE-EAR ELECTROENCEPHALOGRAPHY SYSTEM WITH FLOATING ELECTRODES AND METHOD THEREOF

CROSS-REFERENCE TO RELATED APPLICATIONS

There are no cross-related applications.

FIELD OF THE INVENTION

The present invention generally relates to systems and method to detect bioelectrical signals. More particularly, the present invention relates to systems and method for recording bioelectrical signals using floating electrodes.

BACKGROUND OF THE INVENTION

Bioelectrical signals are generally understood as electrical potential differences originating from a living body. Well-known examples are Electrocardiogram (ECG) signals and Electroencephalogram (EEG) signals. An ear component for detecting bioelectrical signals at the ear is often made for the detection of EEG signals, but could also be applied for detecting other bioelectrical signals such as ECG, electrooculography (EOG), or muscular activity.

Many recording systems uses EEG recording technology to capture bioelectric signals from a user. In some applications, the signals captured by EEG recording technologies are used for brain-computer interfaces (BCI), vital sign monitoring or any other methods or systems using bioelectric signals as input.

Many systems use EEG recording technologies. For instance, Kidmose et al. describe in US Patent publications 2012/0123290 and 2012/0302858 an EEG monitoring system adapted to be carried continuously by a person to be monitored. The system has an implant unit that is located subcutaneously behind the ear of a patient. The implant unit has an electronics part and two electrodes for picking up electrical EEG signals from the brain of the patient. The electronics part has the necessary electronics for sampling the EEG signals measured by the electrodes and transmitting them wirelessly to an external monitoring unit. The monitoring unit resembles a behind-the-ear hearing aid having an earplug and a housing that is placed behind the ear. The housing has a processing unit adapted to receive wirelessly the EEG readings from the implant unit. The housing is connected to the earplug via a sound tube or an electric cord leading to a receiver of the earplug. This allows the monitoring unit to transmit messages, such as alarms or warnings, into the ear of the person carrying the EEG monitoring system. Despite the portability of the system, this system requires surgery to position the electrodes and the electronics part subcutaneously behind the ear of the patient and is invasive. Moreover, the patient cannot easily remove the implant unit at his own will.

In U.S. Pat. No. 9,408,552 to Kidmose et al., there is described an earplug having a shell with at least two electrodes adapted to measure brain wave signals. The electrodes are positioned on a contour portion of the shell and are connected to a processor for measuring the signals. The shell is shaped to individually match at least part of the ear canal and the concha of the user. The earplug is connected to a behind-the-ear component and the brain wave signals detected by the electrodes of the earplug are transmitted to the behind-the-ear component for further processing. The shell is made from a flexible material such as plastic or silicon. The electrodes are positioned on or integrated within the surface of the shell and counts at least one reference electrode and at least one detecting electrode. Kidmose et al. present an earplug having more or less five electrodes. The electrodes are made from alloys such as stainless steel, platinum-iridium or noble metals such as silver, gold, titanium, platinum and tungsten. Otherwise, the electrodes can also be made from silver-silver chloride. In order to improve the quality of the signals detected by the electrodes, a conductive gel is applied. Although Kidmose et al. describe a portable and non-invasive brain wave signal measuring device, since the active electrode or captor electrode is positioned in proximity with the reference electrode, the electrodes can only measure localised brain activity produced by cortex generators that are in proximity with the outer ear-canal and may not be appropriate for providing general or extensive brain activity readings. Furthermore, Kidmose et al. requires the use of gel to improve the quality of the contact.

In US Patent Application published under No. US 2017/0281037A1, Kidmose et al. describe an active electrode for sensing an electric potential and generating an input signal. Kidmose et al. discloses an EEG device comprising two electrodes fixed to the outer surface of the EEG device to form the active electrodes. As the electrodes are not moving with regard to the periphery of the EEG device, the contact formed in the ear canal may be of lower quality and thus producing a non-negligible level of noise in the captured signal.

In US Patent Application published under No. US 2018/0177421 A1, Kilsgaard et al. describe an EEG monitoring device coupled to an ear canal of a user. The device comprises an ear insert having capacitive electrodes installed on flanges extending outward from the sound channel. The flanges are made of flexible material to conform with the shape of the ear canal of the user. Such products comprising flanges are known to be uncomfortable to the user and to provide a reduced attenuation, usually because the contact between the flanges and the ear canal is perfectible. Also, such device requires capacitive electrodes having a dielectricum.

In European patent application published under no. EP 3 181 041 A1, Philips N.V. discloses an EEG ear insert comprising a portion formed a sensor made from conductive rubber, conductive silver textile, a silicone material and/or other materials. Such ear insert may have reduced conductivity, may be uncomfortable to the wearer and does not allow capturing biologically-relevant information associated with a user and audio protection. Also, no other electrodes are disclosed, such as electrodes positioned around the ear, thus limiting field of usage of such ear insert.

In U.S. Pat. No. 10,213,157, Farrell et al. disclose a wearable audio product for obtaining biologically-relevant information associated with a user. The product comprises two electrodes, a first electrode outside of the ear canal and a second electrode placed inside an ear canal of the user. The product comprises a "C" shaped clip hooked behind the ear of a user and an ear tip to be inserted in the ear, the ear tip being made of flexible material. Embodied as glasses or headband, the wearable product is fairly large which generally requires many electrodes. Embodied as small factor, the pressure applied on the electrode is reduced thus reducing utility of the capture biological signal. As no biological signal is capture within the ear, such product may not be used to identify muscle movements.

In US Patent Application published under no. 2019/0053756 A1, Ayers et al. discloses an audio product for obtaining biologically-relevant information associated with a user. The product comprises an earpiece having a flexible coated ear tip and a tail portion. The ear tip has an umbrella shaped tip. Such ear insert may have reduced conductivity, may be uncomfortable to the wearer and does not allow capturing biologically-relevant information associated with a user and audio protection. Such audio product is also limited to a single electrode by ear when the tip is coated or made of conductive silicone.

SUMMARY OF THE INVENTION

The shortcomings of the prior art are generally mitigated by an ear and around-the-ear electroencephalography system with floating electrodes and method thereof.

In one aspect of the invention, a floating electrode for reading bioelectric signal from a biological canal is provided. The floating electrode comprises a plurality of floating conductive wires, each floating conductive wire being attachable to an insert adapted to be inserted in the biological canal and being in communication with a signal processor, the electrode being adapted to move when squeezed between the biological canal and an outskirt of a portion of the insert being inside the biological canal.

Even if the text refers to floating conductive wires, it shall be understood that the conductive wires may also be fixed, deformable, flexible, elastic, rigid, conductive, capacitive, etc.

Each conductive wire may be attachable to the insert at only one of the extremities of the conductive wire or each conductive wire may be made of alloys or noble metals. The biological canal may be an ear canal.

In another aspect of the invention, a plug for a biological canal comprising a floating electrode is provided. The plug comprises an inner portion to be inserted into the biological canal and an outer portion. The floating electrode comprises a floating conductive wire, the floating conductive wire being attached to the inner portion of the plug, disposed over the outskirt of the outer portion and in communication with a signal processor. The electrode is adapted to move on the outskirt of the outer portion when squeezed between the biological canal and the outskirt of the inner portion being inside the biological canal.

The inner portion may be made of a squeezable yet resilient bio-compatible material. The inner portion may have a volume larger than the volume of portion of the biological canal in which the inner portion is inserted. The inner portion may be a custom fit to the biological canal and the biological canal may be an ear canal for which the plug may be an earplug.

In yet another aspect of the invention, a floating electrode for reading a bioelectric signal from skin around an organ, the floating electrode comprising a floating conductive portion being connectable to a signal processor, a resilient portion adapted to expand and retract the floating conductive portion and a non-conductive linking portion attached to the flexible conductive portion. The flexible, resilient and non-conductive linking portions form an expandable loop around the organ.

The organ may be an ear. The conductive portion may be made of alloys or noble metals. The floating electrode may further comprise a second floating conductive portion, the non-conductive linking portion being connected at each end to the one of the two conductive portions. The floating electrode may further comprise a second resilient portion adapted to expand and retract the second floating conductive portion. The non-conductive linking portion and the resilient portion may be integral.

In another aspect of the invention, a system for reading bioelectric signal from the skin of a user is provided. The system comprises a signal processor, a plug for inserting in a biological canal. The plug comprises an inner portion to be inserted into the biological canal, an outer portion and an inner floating electrode comprising a floating conductive wire, the floating conductive wire being attached to the inner portion of the plug, disposed over the outskirt of the outer portion and in communication with the signal processor. The floating electrode is adapted to move on the outskirt of the outer portion when squeezed between the biological canal and the outskirt of the inner portion being inside the biological canal.

The system further comprises an outer floating electrode for reading a bioelectric signal from skin around an organ, the floating electrode comprising a flexible conductive portion connected to the plug and being in communication with the signal processor, a resilient portion adapted to expand and retract the flexible conductive portion and a non-conductive linking portion attached to the flexible conductive portion. The flexible, resilient and non-conductive linking portions form an expandable loop around the organ starting from the plug.

The organ may be an ear. The conductive portion and the inner floating electrode may be made of alloys or noble metals. The floating electrode further comprises a second flexible conductive portion, the non-conductive linking portion being connected at each end to the one of the two conductive portions.

In a further aspect of the invention, a method to fit the above described system to the user is provided. The method comprises inserting the plug within the biological canal of the user, extending the outer floating electrode to form a loop large enough to insert the organ within the formed loop and releasing the outer floating electrode around the organ.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which.

DETAILED DESCRIPTION OF THE PREFERRED EMBODIMENT

A novel in-ear and around-the-ear electroencephalography system with floating electrodes and method thereof will be described hereinafter. Although the invention is described in terms of specific illustrative embodiments, it is to be understood that the embodiments described herein are by way of example only and that the scope of the invention is not intended to be limited thereby.

Figure 1:
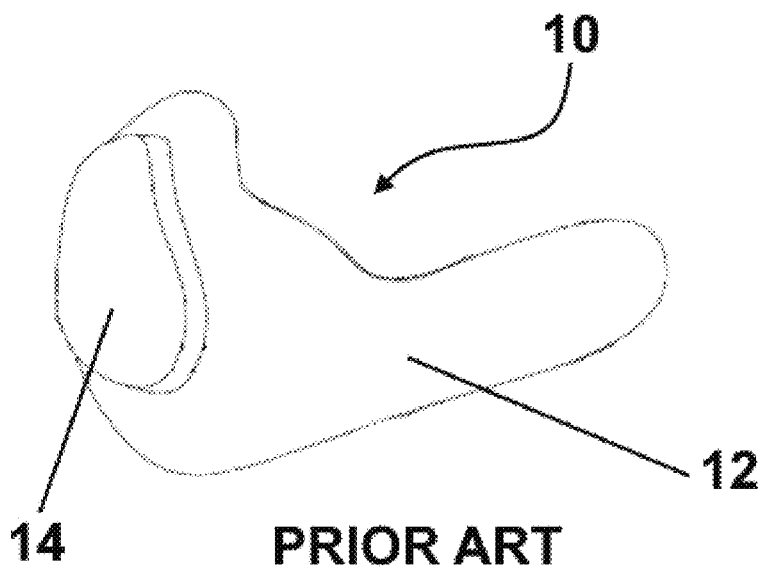
FIG. 1 is a side view of an earplug as seen in the prior art.

Referring to FIG. 1, an earplug 10 as typically used in the prior art is shown. The earplug comprises an inner portion 12 adapted to be inserted into an ear canal 32 (see FIG. 3) and an outer portion 14 generally adapted to receive any electronics or device configured to process or transfer a captured bioelectric signal.

Figure 2:
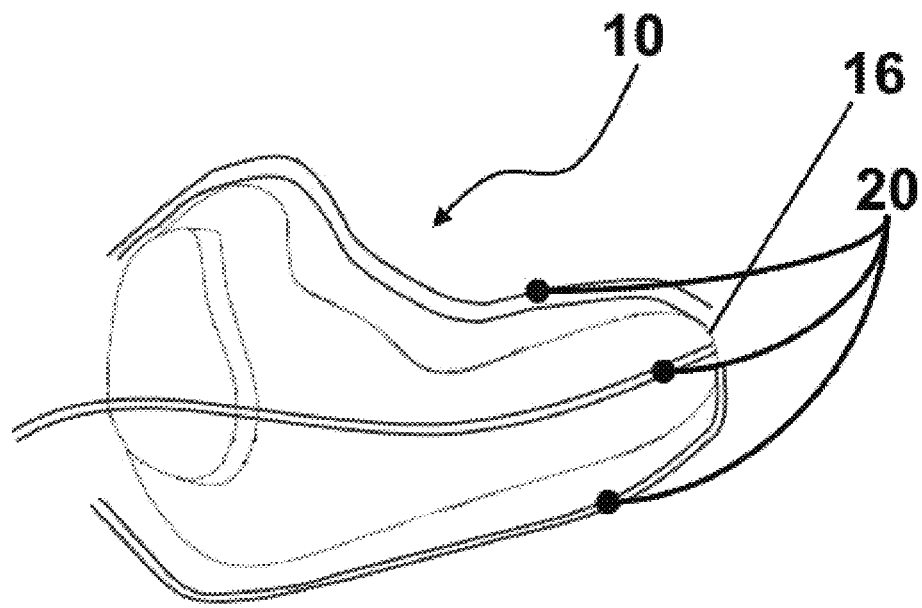
FIG. 2 is a side view of an earplug comprising intra-auricular floating electrode wires in accordance with the principles of the present invention.

Referring to FIG. 2, an earplug 10 comprising intra-auricular floating electrode 20 is shown. The floating electrodes 20 are typically wires or cables made of a skin conductive material and of a material allowing to conform with the shape of the inner portion 12 of the ear plug 10.

Typically, an electrode 20 creates a conductive pathway from the skin of the user to the electrode 20. To ensure a reliable conductive pathway, the electrode may be pressed again the skin. Understandably, even if dry-contact electrodes are preferred in the present disclosure, one skilled in the art shall understand that any type of electrodes 20 capturing bioelectric signal may be used within the scope of the present invention.

Each floating electrode 20 is installed or attached from an innermost extremity 16 of the inner portion 12 to the outer portion 14. In some embodiments, an end of the floating electrode 20 is glued or mounted to the innermost extremity 16. Also, an end of the floating electrode 20 may be glued to a rigid ring which in turn is fixed or glued to the inner most portion 16 of the outer portion 14.

Figure 3:
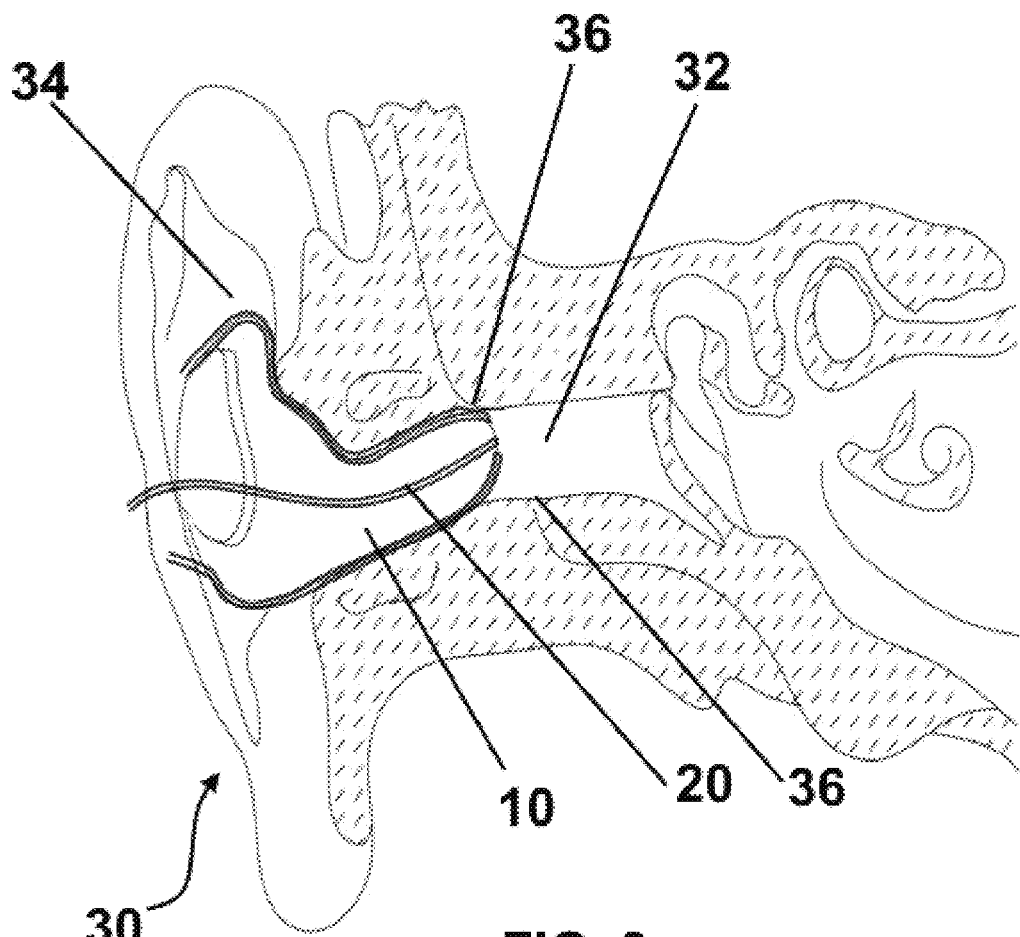
FIG. 3 is a side view of an earplug comprising intra-auricular floating electrode wires inserted in the ear canal in accordance with the principles of the present invention.
Figure 4:
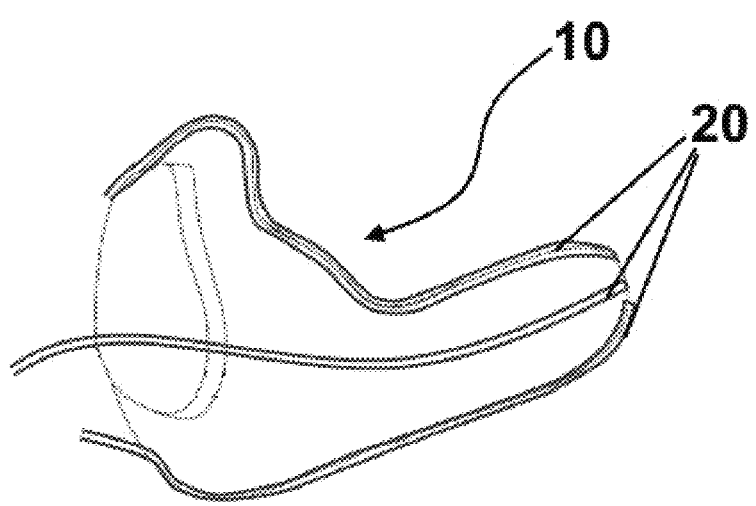
FIG. 4 is a side view of the earplug of FIG. 2 being custom shaped for an ear.

In some embodiments, as the embodiment shown in FIGS. 1 to 3, the inner portion 12 of the earplug 10 is custom fitted to the user ear canal. Understandably, any known method or any methods to be develop to custom fit the inner portion 12 to the ear canal 32 may be used within the scope of the present invention. Thus, in such embodiments, the floating electrodes 20 are disposed over the inner portion 12 of the earplug 10. As the inner portion 12 is inflated or compressed to fit the ear canal 32 of a user, the floating electrodes 20 are moved to conform with the new custom shape of the periphery of the inner portion 12 (see FIG. 4). As the earplug 10 is inserted into the ear canal, the electrodes 20 are pressed or pinched between the ear canal 32 and the inner portion 12 of the earplug 10. Such pression is enough to generate a good contact with the skin of the user within the ear canal 32. In a typical embodiment, bioelectric signals are captured by the electrodes 20 and processed by a controller within the outer portion 14 of the earplug 10.

Referring now to FIG. 3, the earplug 10 is shown inserted in the ear 30 of a user. As shown, the inner portion 12 of the earplug 10 is pressed against the wall 36 of the ear canal 32 and thus creating a contact. The outer portion 14 generally protrudes from or is within the auricle 34 of the ear 30.

The floating electrodes are typically made from biological conductor material, from alloys such as stainless steel, platinum-iridium or from noble metals such as but not limited to silver, titanium, platinum and tungsten. precious metals.

Figure 5:
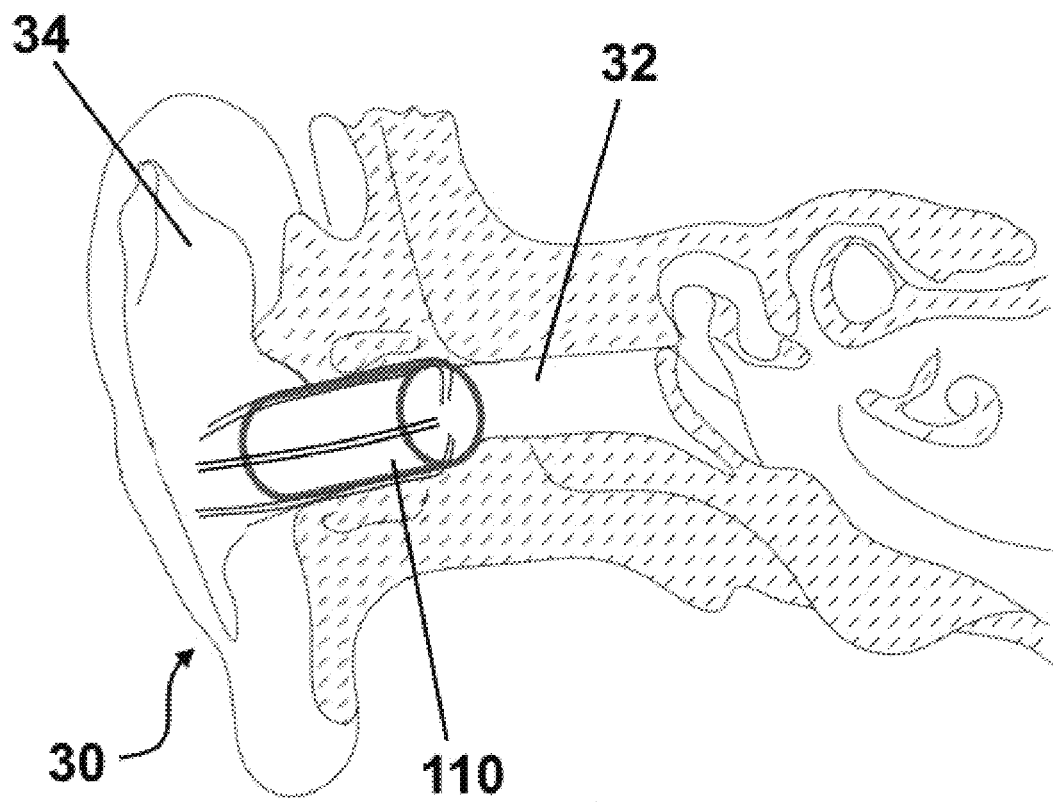
FIG. 5 is a side view of a generic earplug comprising intra-auricular floating electrode wires inserted in the ear canal in accordance with the principles of the present invention.
Figure 6:
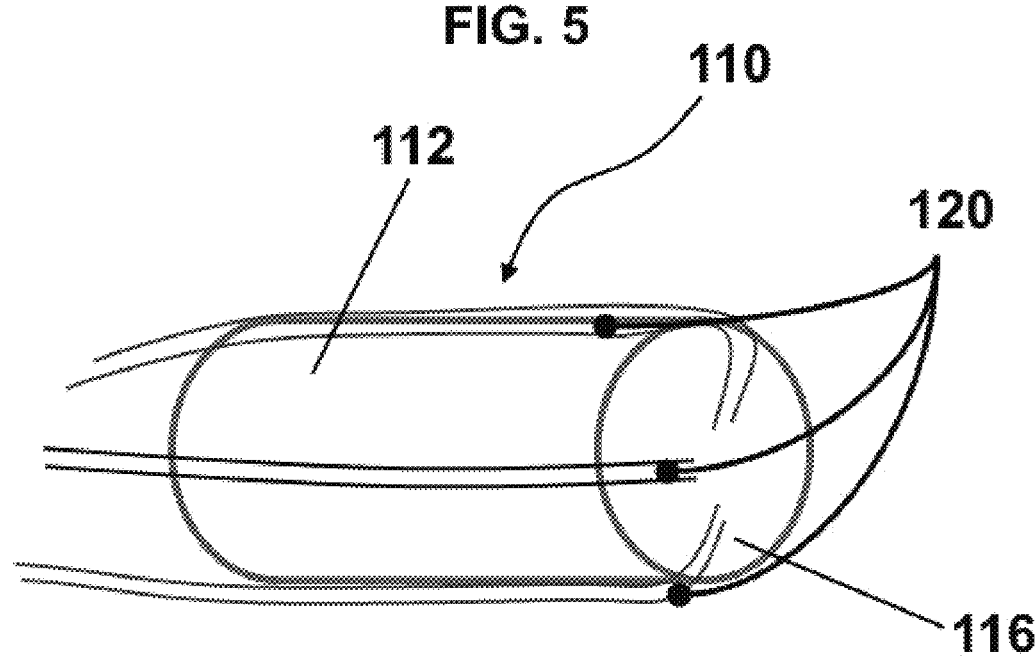
FIG. 6 is a side view of the earplug of FIG. 5.

Referring now to FIGS. 5 and 6, another embodiment of a generic earplug 110 is illustrated inserted within the ear 30 (FIG. 5) and outside of an ear 30 (FIG. 6). In such embodiments, the earplug 110 generally has a rounded cylindrical shape. Understandably, such earplug 110 has a generic shape which tend to have reduced fit within the ear canal 32 of the ear 30 of a user. In such an embodiment, floating electrodes 120 are attached to the inner most end 116 of the ear plug 110. The inner portion 112 of the earplug 110 may have a volume greater than the volume of the ear canal 32 and be made of compressible and/or deformable material. In such embodiments, as the inner portion 112 is inserted in the ear canal 32, the inner portion 112 is compressed against inner wall 36 of the ear canal 32, thus pressing the electrodes 120 against the said inner wall 36 to create a contact allowing capturing a bio signal.

Figure 7:
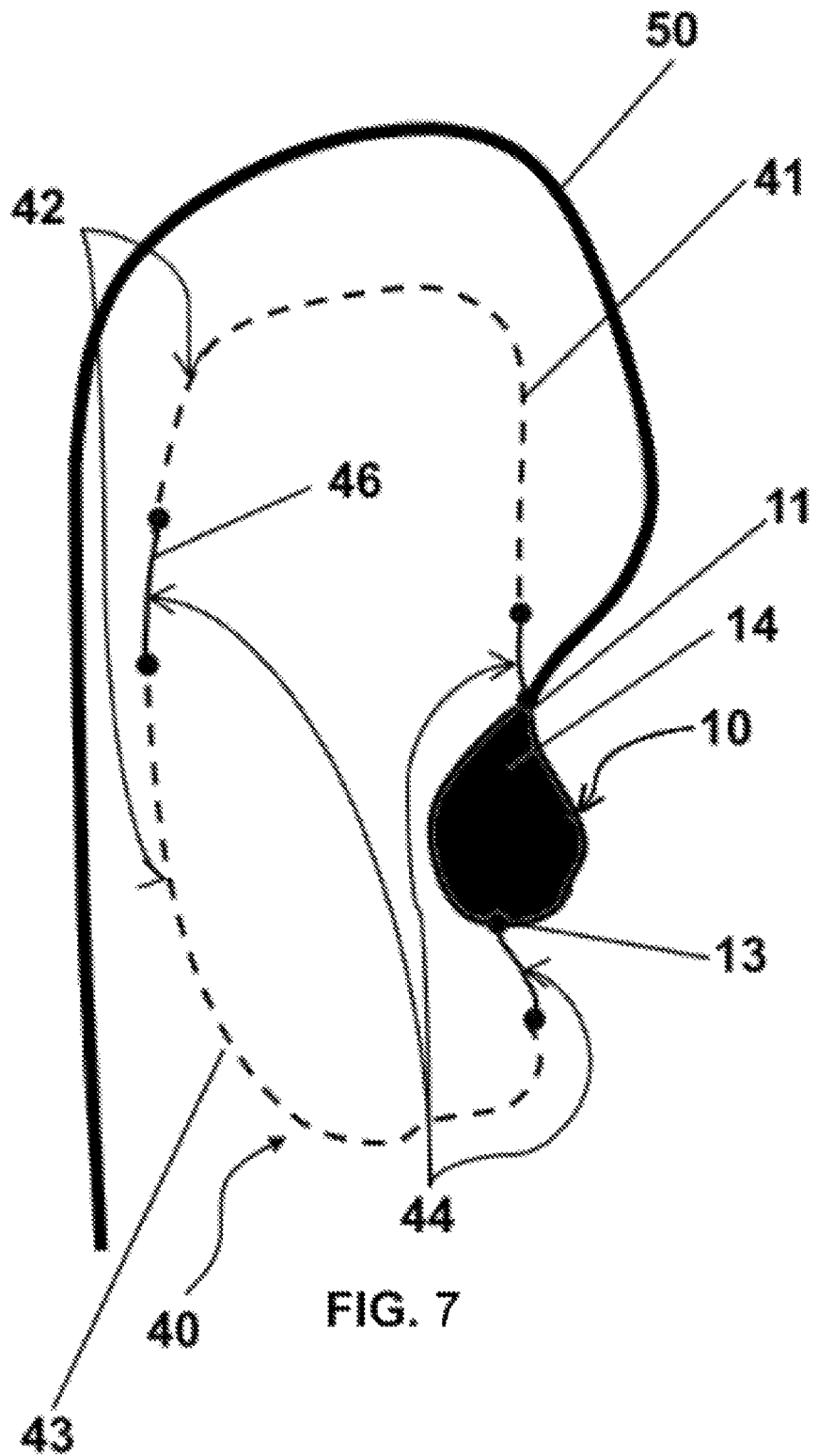
FIG. 7 is a side view of an around the ear electroencephalography system comprising floating electrode wires in accordance with the principles of the present invention.
Figure 8:
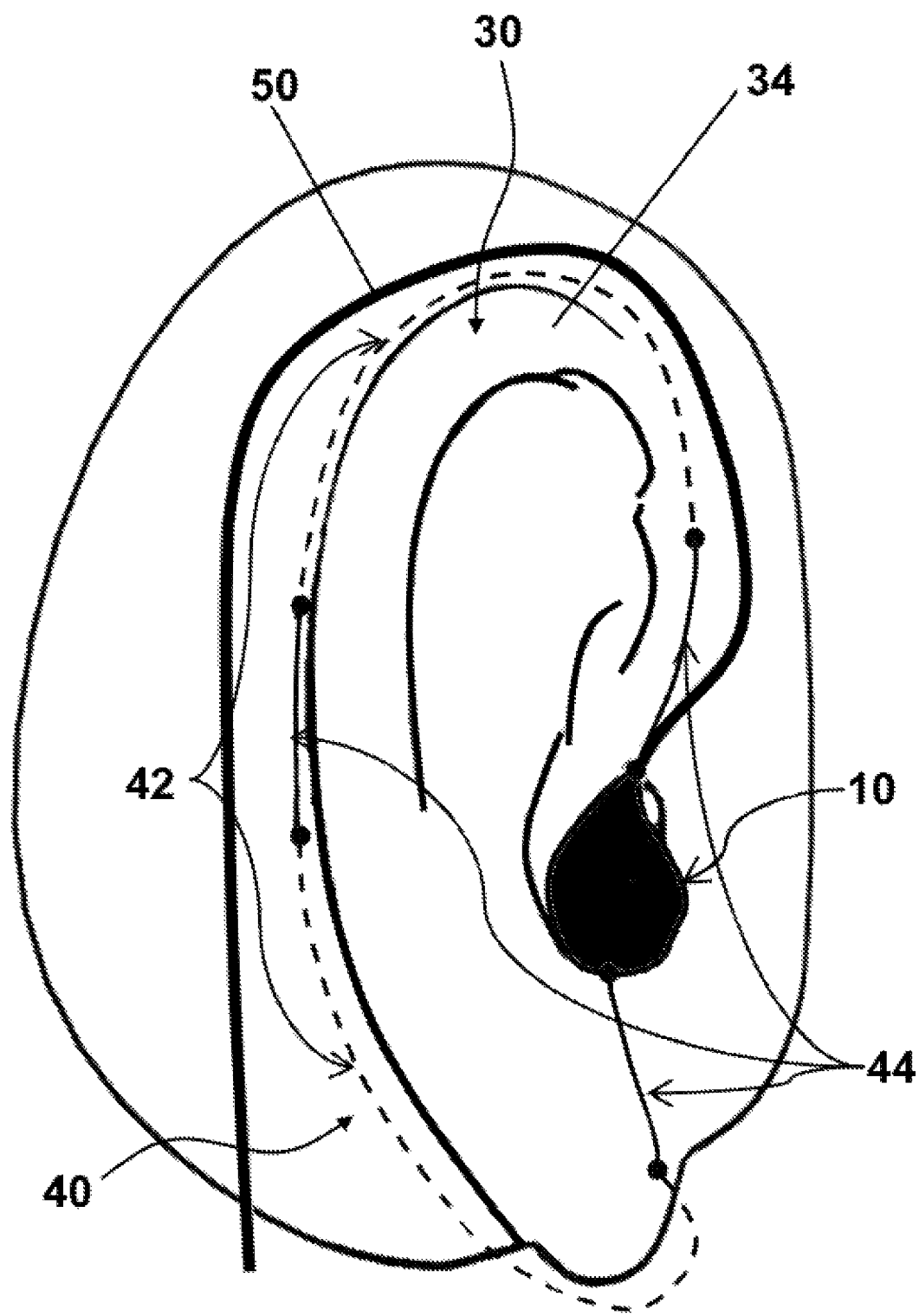
FIG. 8 is a side view of the around the ear electroencephalography system of FIG. 7 shown attached in an ear.

Referring now to FIGS. 7 and 8, an embodiment of an around the ear electroencephalography (EEG) system is shown. The around the ear EEG system comprises an around the ear component 40 comprising at least one conducting non-extendable portion 42 and at least one resilient non conductive portion 44. The conductive portions 40 generally comprise a first conductive portion 41 connected to a first connector 11 of the controller of the earplug 10 and a second conductive portion 43 connected to a second connector 13 of the controller of the earplug 10. The first 41 and second 43 conductive portions are connected together at their free extremity by a connecting non-conductive portion 46. The connecting non-conductive portion 46 must be made of non-conductive material but may be made of resilient or rigid material, such as rubberized wire, fishing line, etc.

In some embodiments, the controller may comprise a signal processor, a power supply, a microphone, a loudspeaker or any other electronic equipment. Understandably, the controller may be located within the earplug 10 or outside of the ear plug 10, such as attached to the hook 50 or to the outer portion 14 of the earplug 10.

The around the ear component 40 comprises at least one resilient or extendable portion 44 allowing the around the ear component 40 to be extended around the auricle 34 of the ear 30 yet to be contact behind the ear 30 of the user. As such, the resiliency of the resilient portion 44 of the around the ear component 40 creates a pression behind the ear 30 of the user thus creating a connection with the skin of the user.

In some embodiments, the resilient portions 44 may be made of a non-extendable conductive wire inserted in a resilient housing, such as a rubber cover. In some embodiments, the length of the non-extendable conductive wire is greater than the length of resilient housing to allow the cable be tightened when the housing is extended. Understandably, any other method to provide a resilient outer portion to an inner conductive portion may be used within the scope of the present invention.

In a typical embodiment, the around the ear component 40 comprises an upper conductive portion 41, a lower conductive portion 43, a non-conductive or isolating portion 46 between the upper and lower portions 41, 43 and an elastic or resilient portion 44 between one of the upper or lower conductive portions 41, 43.

In another embodiment, the around the ear component 40 may further comprise a second resilient portion between the lower or upper conductive portions 43, 41.

The EEG system may further comprise a hook portion 50 extending from or connected to the outer portion 14 of the ear plug 10. The hook portion 50 is generally positioned behind the ear 30 of the user and may be made of rigid or semi-rigid material.

In some embodiments, the hook portions 50 may be adapted to receive or mount any cables extending from the controller of the earplug 10. In yet other embodiments, the hook portions 50 may be integrated or connected to the around-the-ear component 40 or may be one of the portions of the around-the-ear component 40.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A floating electrode for reading bioelectric signal from a biological canal, the floating electrode comprising a plurality of flexible conductive wires in communication with a signal processor, a portion of each flexible conductive wire being attached to an insert adapted to be inserted in the biological canal, a free floating portion of the flexible conductive wires being capable of independent movement in any direction over an outer surface of the insert when squeezed between the biological canal and the outer surface of a portion of the insert being inside the biological canal.

2. The floating electrode of claim 1, each conductive wire being attached to the insert at only one of the extremities of the conductive wire.

3. The floating electrode of claim 1, each conductive wire being made of alloys or noble metals.

4. The floating electrode of claim 1, the biological canal being an ear canal.

5. A plug for a biological canal comprising a floating electrode, the plug comprising:
   an inner portion to be inserted into the biological canal;
   an outer surface;
   the floating electrode comprising a flexible conductive wire in communication with a signal processor, the flexible conductive wire comprising:
   a first portion attached to the inner portion of the plug and a free floating portion disposed over the outer surface of the plug;
      wherein the free floating portion is capable of independent movement in any direction over the outer surface when squeezed between the biological canal and the outer surface being inside the biological canal.

6. The plug of claim 5, the inner portion being made of a squeezable yet resilient material.

7. The plug of claim 5, the inner portion having volume larger than the volume of portion of the biological canal in which the inner portion is inserted.

8. The plug of claim 5, the inner portion being custom fit to the biological canal.

9. The plug of claim 5, the biological canal being an ear canal.

10. The plug of claim 5, the plug being an earplug.

11. A floating electrode for reading a bioelectric signal from skin around an organ, the floating electrode comprising:
    a flexible conductive portion connectable to a signal processor and;
    a resilient portion attached to the flexible conductive portion and adapted to expand and retract the flexible conductive portion;
    a non-conductive linking portion attached to the flexible conductive portion;
    the flexible, resilient and non-conductive linking portions forming an expandable loop around the organ.

12. The floating electrode of claim 11, the organ being an ear.

13. The floating electrode of claim 11, the conductive portion being made of alloys or noble metals.

14. The floating electrode of claim 11, the floating electrode further comprising a second flexible conductive portion, the non-conductive linking portion being connected at each end to the one of the two conductive portions.

15. The floating electrode of claim 14, the floating electrode further comprising a second resilient portion adapted to expand and retract the second flexible conductive portion.

16. The floating electrode of claim 11, the non-conductive linking portion and the resilient portion being integral.

17. A system for reading bioelectric signal from the skin of a user, the system comprising:
    a signal processor;
    a plug for inserting in a biological canal, the plug comprising:
       an inner portion to be inserted into the biological canal comprising an outer surface;
       an inner floating electrode comprising a flexible conductive wire, the flexible conductive wire being:
       attached to the plug;
       disposed over the outer surface;
       in communication with the signal processor,
    wherein the flexible conductive wire is adapted to move over the outer surface when squeezed between the biological canal and the outer surface of the inner portion being inside the biological canal:
    an outer floating electrode for reading a bioelectric signal from skin around an organ, the floating electrode comprising:
       a flexible conductive portion connected to the plug and being in communication with the signal processor;
       a resilient portion attached to the flexible conductive portion and adapted to expand and retract the flexible conductive portion;
       a non-conductive linking portion attached to the flexible conductive portion;
    the flexible, resilient and non-conductive linking portions forming an expandable loop around the organ starting from the plug.

18. The system of claim 17, the organ being an ear.

19. The system of claim 17, the conductive portion and the inner floating electrode being made of alloys or noble metals.

20. The system of claim 17, the floating electrode further comprising a second flexible conductive portion, the non-conductive linking portion being connected at each end to the one of the two conductive portions.

21. A method to fit the system of claim 17 to a user, the method comprising:
    inserting the plug within the biological canal of the user;
    extending the outer floating electrode to form a loop large enough to insert the organ within the formed loop;
    releasing the outer floating electrode around the organ.

* * * * *